United States Patent
Sano et al.

(10) Patent No.: US 12,201,428 B2
(45) Date of Patent: Jan. 21, 2025

(54) BIOMEDICAL ELECTRODE PAD, BIOLOGICAL SIGNAL PROCESSING DEVICE, AND COMBINATION THEREOF

(71) Applicants: NIPRO CORPORATION, Osaka (JP); HARADA ELECTRONICS INDUSTRY CO., LTD., Sapporo (JP)

(72) Inventors: Yoshihiko Sano, Osaka (JP); Masahide Harada, Sapporo (JP)

(73) Assignees: NIPRO CORPORATION, Osaka (JP); HARADA ELECTRONICS INDUSTRY CO., LTD., Sapporo (JP)

( * ) Notice: Subject to any disclaimer, the term of this patent is extended or adjusted under 35 U.S.C. 154(b) by 748 days.

(21) Appl. No.: 17/041,255

(22) PCT Filed: Mar. 13, 2019

(86) PCT No.: PCT/JP2019/010384
§ 371 (c)(1),
(2) Date: Sep. 24, 2020

(87) PCT Pub. No.: WO2019/188311
PCT Pub. Date: Oct. 3, 2019

(65) Prior Publication Data
US 2021/0007623 A1 Jan. 14, 2021

(30) Foreign Application Priority Data
Mar. 28, 2018 (JP) .................................. 2018-061754

(51) Int. Cl.
*A61B 5/282* (2021.01)
*A61B 5/257* (2021.01)

(52) U.S. Cl.
CPC .............. *A61B 5/257* (2021.01); *A61B 5/282* (2021.01); *A61B 2560/0214* (2013.01); *A61B 2562/0215* (2017.08); *A61B 2562/222* (2013.01)

(58) Field of Classification Search
CPC . A61B 5/282; A61B 5/259; A61B 2562/0215; A61B 2560/0214; A61B 2562/222
See application file for complete search history.

(56) References Cited

U.S. PATENT DOCUMENTS 5,724,984 A * 3/1998 Arnold .................... A61B 5/25
600/382
2008/0139953 A1* 6/2008 Baker .................... A61B 5/024
600/509

(Continued)

FOREIGN PATENT DOCUMENTS

CN 103226996 A 7/2013
CN 103945759 A 7/2014
(Continued)

OTHER PUBLICATIONS

Feb. 7, 2023 Office Action issued in Japanese Patent Application No. 2020-509879.
(Continued)

*Primary Examiner* — Adam Z Minchella
(74) *Attorney, Agent, or Firm* — Oliff PLC

(57) ABSTRACT

A biomedical electrode including: an attachment sheet being elastically stretchable and contractible with an electrically insulating property on a back surface side, an adhesive surface suitable for attachment to the skin; a plurality of electrodes located apart from one another on the back surface side of the attachment sheet and exposed on the back surface side; a plurality of connecting parts located at a central part on the back surface side of the attachment sheet and covered with electrical insulation while being exposed (Continued)

toward a front surface side through openings of the attachment sheet; and electrode connecting wires located on the back surface side of the attachment sheet and covered with electrical insulation that electrically connect respective ones of the plurality of electrodes with corresponding ones of the plurality of connecting parts, wherein at least one of the electrode connecting wires extends in a stretchable, contractible, and bendable manner.

20 Claims, 11 Drawing Sheets

(56) References Cited

U.S. PATENT DOCUMENTS

| | | | |
|---|---|---|---|
| 2008/0154110 A1* | 6/2008 | Burnes | A61B 5/282 600/382 |
| 2010/0228113 A1* | 9/2010 | Solosko | A61N 1/048 600/382 |
| 2012/0035435 A1* | 2/2012 | Choi | A61B 5/6831 600/382 |
| 2013/0192887 A1 | 8/2013 | Yaguchi et al. | |
| 2014/0206977 A1* | 7/2014 | Bahney | A61B 5/25 600/386 |
| 2014/0288407 A1 | 9/2014 | Sano et al. | |
| 2015/0351690 A1* | 12/2015 | Toth | A61B 5/14542 600/391 |
| 2018/0020982 A1 | 1/2018 | Elsherbini et al. | |
| 2018/0235501 A1* | 8/2018 | Nishimura | H01R 13/6581 |
| 2018/0235502 A1 | 8/2018 | Nishimura et al. | |

FOREIGN PATENT DOCUMENTS

| | | |
|---|---|---|
| EP | 3 415 021 A1 | 12/2018 |
| JP | 2009-240623 A | 10/2009 |
| WO | 2017/043595 A1 | 3/2017 |
| WO | 2017/138388 A1 | 8/2017 |
| WO | 2018/012142 A1 | 1/2018 |

OTHER PUBLICATIONS

Denshi; "Holter Electrocardiography Equipment Connection Guide" and "Lead, Relay, and Electrode Cords for Holter Electrocardiography;" Holter Electrocardiography-Related Products; pp. 61 and 65, respectively; downloaded on Feb. 15, 2018; http://www.fukuda.co.jp/medical/products/holter_ecg/pdf/holter_ecg.pdf.
Denshi; "Digital Holter Recorder FM-190;" downloaded on Feb. 19, 2018; http://www.fukuda.co.jp/medical/products/holter_ecg/fm_190.html.
May 21, 2019 Search Report issued in International Patent Application No. PCT/JP2019/010384.
Nov. 30, 2021 Extended European Search Report issued in Patent Application No. 19775809.7.
Feb. 1, 2024 Office Action issued in Chinese Patent Application No. 201980020995.9.
A concise explanation of the relevance of one or more non-English language reference cited herein, in accordance with 37 CFR § 1.98(a)(3)(i), appears in the Appendix attached. See Reference NPL cite 1. That is, the English translation search report is a concise explanation of the Relevance of the Chinese Office Action.
With respect to the following foreign language documents, for which a translation is not submitted: NPL. cite 1 U.S. Pub. cite 1 NPL. cite 1 U.S. Pub. cite 2.

* cited by examiner

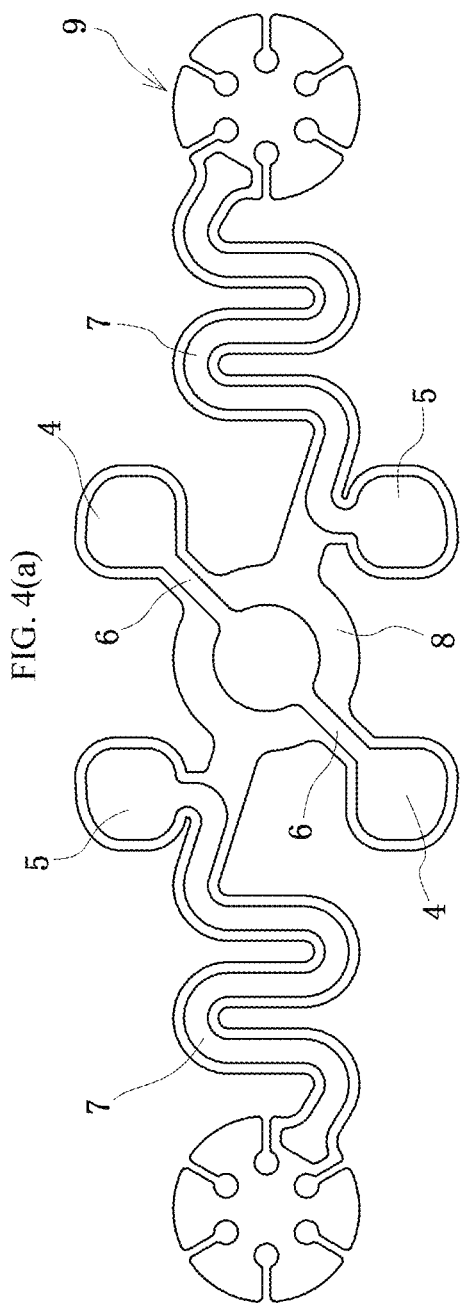
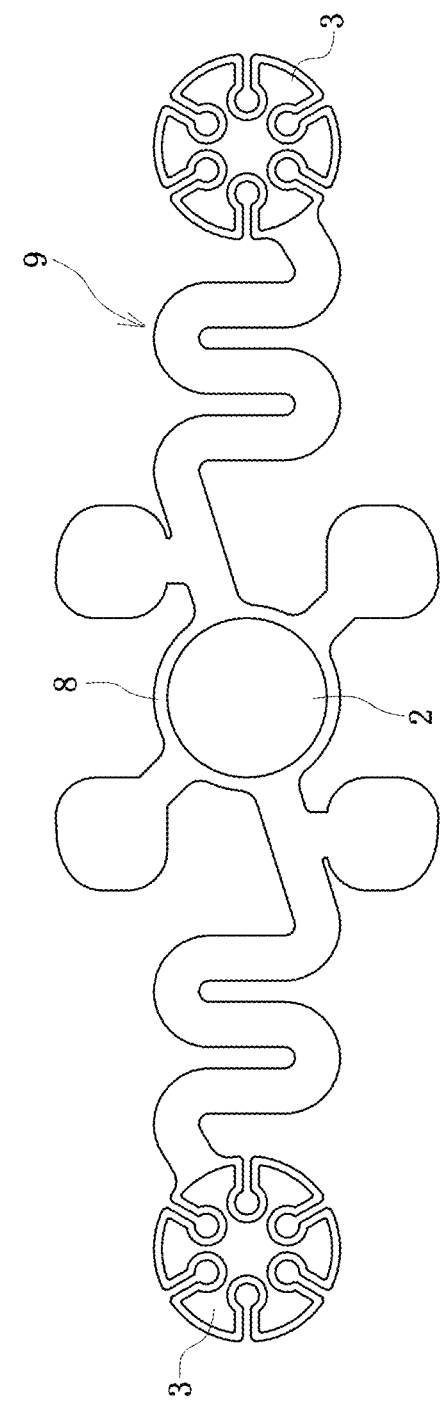
FIG. 4(a)
FIG. 4(b)

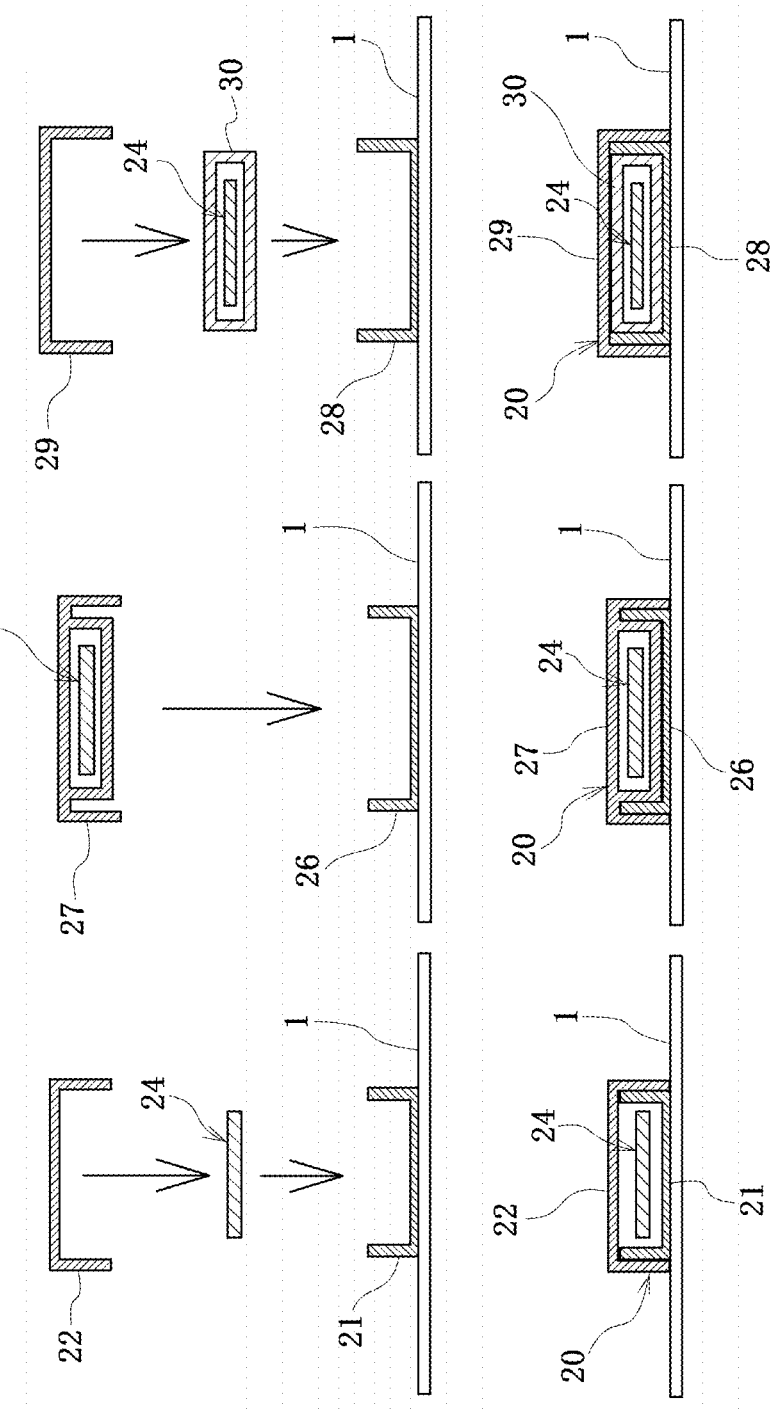

BIOMEDICAL ELECTRODE PAD, BIOLOGICAL SIGNAL PROCESSING DEVICE, AND COMBINATION THEREOF

TECHNICAL FIELD

The present invention relates to a biomedical electrode pad that is attached to the skin of a living body to detect biological electrical signals, such as electrocardiographic signals or myoelectric signals, from the skin, and to a biological signal processing device that performs processing including recording and outputting the biological signals detected by the biomedical electrode pad.

BACKGROUND ART

Examples of hitherto known biomedical electrode pads that are attached to the skin of a living body to detect biological electrical signals from the skin include Fukuda Denshi's event-specific waterproof Excerode E (TEC-07DEW) described in Non Patent Literature 1. This biomedical electrode pad is connected to a portable Holter electrocardiograph and used to monitor events by Holter electrocardiography. It has an attachment sheet of a laterally elongated elliptical shape slightly wider at a central part, and on a lower surface of this attachment sheet, which is an adhesive surface, two detecting electrodes are disposed at both ends in a longitudinal direction, with one indifferent electrode at the center interposed therebetween. An electrode connecting pattern made of conductive metal is extended in a straight line from each electrode to near a side end of the central part of the attachment sheet, and three leads extending from a base end of a composite lead having connectors at leading ends are respectively connected to the electrode connecting patterns.

Examples of hitherto known biological signal processing devices that perform processing including recording and outputting biological signals detected by a biomedical electrode pad like the one described above include Fukuda Denshi's portable Holter electrocardiograph (FM-190) described in Non Patent Literature 2. This Holter electrocardiograph is housed in a portable case, and has the connectors of the composite lead of the above-described biomedical electrode pad connected thereto so as to be electrically connected to the three electrodes through the composite lead and the electrode connecting patterns. The portable case is worn around the arm of a living body, such as a patient to be examined by Holter electrocardiography, by a belt.

CITATION LIST

Non Patent Literature

Non Patent Literature 1: "Holter Electrocardiography Equipment Connection Guide" and "Lead, Relay, and Electrode Cords for Holter Electrocardiography" on pages 61 and 65, respectively, of "Holter Electrocardiography-Related Products," Fukuda Denshi, downloaded on Feb. 15, 2018 from http://www.fukuda.co.jp/medical/products/holter_ecg/pdf/holter_ecg.pdf.

Non Patent Literature 2: "Digital Holter Recorder FM-190," Fukuda Denshi, downloaded on Feb. 19, 2018 from http://www.fukuda.co.jp/medical/products/holter_ecg/fm_190.html.

SUMMARY OF INVENTION

Technical Problem

It is difficult to obtain sufficient biological information by the above-described conventional sheet-shaped biomedical electrode pad because of the narrow range of detecting biological signals. Therefore, the present inventors have considered broadening the range of detecting biological signals by expanding the attachment sheet. It turned out, however, that doing so would create new problems: As stretching and contracting of the attachment sheet are restricted by the electrode connecting patterns that are extended in a straight line from both ends of the attachment sheet to near the side ends of the central part, the biomedical electrode pad fails to follow changes in shape of the limb due to body movement and comes easily off the skin. Moreover, the electrode connecting patterns break easily by undergoing excessive local deformation while stretching and contracting so as to follow changes in shape of the limb due to body movement.

Since the above-described conventional portable Holter electrocardiograph that is housed in the portable case worn around the arm of a living body, such as a patient to be examined by Holter electrocardiography, by the belt is connected to the biomedical electrode pad through the composite lead, another problem is that the biomedical electrode pad comes easily off the skin as a tensile force is applied to the leads due to body movement, such as movement of the arm or twisting of the body.

Solution to Problem

The present invention advantageously solves the problems with the above related art. A biomedical electrode pad of the present invention is a biomedical electrode pad that is attached to skin of a living body and used to detect biological electrical signals from the skin, and is characterized by including:

an attachment sheet that is elastically stretchable, contractible, and bendable, has an electrically insulating property, and has, on a back surface side, an adhesive surface suitable to be attached to the skin of a living body;

a plurality of electrodes that are located apart from one another on the back surface side of the attachment sheet and exposed on the back surface side;

a plurality of connecting parts that are located at a central part on the back surface side of the attachment sheet and covered with electrical insulation while being exposed toward a front surface side through openings of the attachment sheet; and electrode connecting wires that are located on the back surface side of the attachment sheet and covered with electrical insulation, and that electrically connect respective ones of the plurality of electrodes with corresponding ones of the plurality of connecting parts, wherein at least one of the electrode connecting wires extends in a stretchable, contractible, and bendable manner.

A biological signal processing device of the present invention is characterized by including:

a casing that is fixed to a central part on a front surface side of an attachment sheet of a biomedical electrode pad, the attachment sheet having, on a back surface side, an adhesive surface suitable to be attached to skin of a living body and a plurality of electrodes;

a biological signal processing circuit board that is housed inside the casing and electrically connected to each of the plurality of electrodes on the back surface side of the biomedical electrode pad through a connecting member extending through the casing and a central part of the attachment sheet, and that processes biological signals detected by the plurality of electrodes and outputs a processing result; and a battery that is housed inside the casing and supplies electricity to the biological signal processing circuit board.

Advantageous Effects of Invention

When the attachment sheet of the biomedical electrode pad of the present invention is attached to a biological signal detecting position in the skin of a subject through the adhesive surface on the back surface side of the attachment sheet, the plurality of electrodes that are located apart from one another on the back surface side of the attachment sheet and exposed on the back surface side detect biological electrical signals from the skin of the subject. These biological signals are transmitted by the electrode connecting wires that are located on the back surface side of the attachment sheet and covered with electrical insulation to the plurality of connecting parts that are located at the central part on the back surface side of the attachment sheet and covered with electrical insulation, and are then output toward the front surface side of the attachment sheet by those portions of the connecting parts that are exposed through the openings of the attachment sheet.

Since the attachment sheet is elastically stretchable, contractible, and bendable and has an electrically insulating property, the attachment sheet remains in close contact with the skin by stretching, contracting, and/or bending so as to follow changes in shape of the limb due to body movement. Moreover, since at least one of the electrode connecting wires that electrically connect respective ones of the plurality of electrodes with corresponding ones of the plurality of connecting parts extends in a stretchable, contractible, and bendable manner, the electrode connecting wires are less likely to break by undergoing excessive local deformation when the attachment sheet stretches, contracts, and/or bends so as to follow changes in shape of the limb due to body movement.

Therefore, even when the attachment sheet is expanded compared with the conventional one to broaden the range of detecting biological signals, the biomedical electrode pad of the present invention can continuously detect biological signals from the skin by the plurality of electrodes for a long period of time, regardless of changes in shape of the limb due to body movement.

In the biological signal processing device of the present invention, when the elastically stretchable and contractible attachment sheet of the biomedical electrode pad is attached to a biological signal detecting position in the skin of a subject through the adhesive surface on the back surface side of the attachment sheet, the biological signal processing circuit board housed inside the casing fixed to the central part on the front surface side of the attachment sheet is electrically connected to each of the plurality of electrodes provided on the back surface side of the biomedical electrode pad through the connecting member extending through the casing and the central part of the attachment sheet. By being supplied with electricity from the battery that is also housed inside the casing, the biological signal processing circuit board processes biological signals detected from the skin of the subject by the electrodes and outputs the processing result by, for example, recording it on a recording medium or wirelessly transmitting it.

Thus, in the biological signal processing device of the present invention, the biological signal processing circuit board is housed inside the casing fixed to the front surface side of the elastically stretchable and contractible attachment sheet of the biomedical electrode pad, supplied with electricity from the battery, and electrically connected to each of the plurality of electrodes on the back surface side of the attachment sheet through the connecting member extending through the casing and the central part of the attachment sheet. Since wires connecting the biological signal processing circuit board and the biomedical electrode pad to each other are not exposed to the outside, the biomedical electrode pad is unlikely to come easily off the skin due to body movement, such as movement of the arm or twisting of the body, and therefore can continuously detect biological signals from the skin by the plurality of electrodes for a long period of time, regardless of changes in shape of the limb due to body movement.

A combination of the biomedical electrode pad of the present invention and the biological signal processing device of the present invention, despite using the biomedical electrode pad of which the attachment sheet is expanded compared with the conventional one to broaden the range of detecting biological signals, can continuously detect biological signals from the skin by the plurality of electrodes for a long period of time, regardless of changes in shape of the limb due to body movement, by effectively preventing the biomedical electrode pad from coming off the skin.

In the biomedical electrode pad of the present invention, a conductive gel sheet may be disposed as a layer on each of the plurality of electrodes. Thus, the electrical resistance between the electrodes and the skin can be reduced by the conductive gel sheets to raise the biological signal detection level. In this case, either the plurality of electrodes or the conductive gel sheets may be disposed on the skin side. In the biomedical electrode pad of the present invention, the plurality of electrodes may include an indifferent electrode and a plurality of detecting electrodes, and thus biological signals can be more easily detected. Further, the electrode connecting wire that extends in a stretchable, contractible, and bendable manner may have a conductor that extends so as to bend in a bellows shape. Alternatively, the electrode connecting wire may have fibrous conductors that are in a form of mesh, a chain, or a cloth, such as a woven cloth or a non-woven cloth, or have a conductor that is made of a conductive rubber-like elastic material. Thus, the electrode connecting wires can easily stretch, contract, and bend along the skin.

In the biomedical electrode pad of the present invention, a cover sheet may be stuck on the back surface side of the attachment sheet, and the electrode connecting wires and the connecting parts may be fixed to the attachment sheet by being covered with the cover sheet. The cover sheet has smaller dimensions than the attachment sheet such that the adhesive surface at a peripheral portion of the attachment sheet is exposed, and has openings through which the plurality of electrodes are respectively at least partially exposed. Thus, the electrode connecting wires and the connecting parts can be easily covered with electrical insulation. At the same time, the electrode connecting wires and the connecting parts can be easily prevented from coming off or shifting over the attachment sheet as a result of the attachment sheet stretching and contracting according to changes in shape of the limb due to body movement.

In the biological signal processing device of the present invention, the connecting member extending through the casing and the central part of the attachment sheet may be electrically in contact with at least either the biological signal processing circuit board or the connecting parts in a separable manner. Thus, the battery and a recording medium can be easily replaced by attaching and detaching the biological signal processing circuit board to and from the casing. In this case, it is preferable that the contact member be contact pins that are erected on the biological signal processing circuit board and extend through the casing in an insertable and extractable manner, because then the biological signal processing circuit board can be easily connected by bringing the contact pins into contact with the connecting parts.

In the biological signal processing device of the present invention, the casing may have a lower casing part that is fixed to the attachment sheet and an upper casing part that is mounted to the lower casing part in a detachable manner, and the lower casing part and the upper casing part may house the biological signal processing circuit board. Alternatively, the casing may have a mounting holder that is fixed to the attachment sheet, and a casing main body that houses the biological signal processing circuit board and is mounted to the mounting holder in a detachable manner, or the casing may have a mounting holder that is fixed to the attachment sheet, a casing main body that houses the biological signal processing circuit board, and a casing cover that covers the casing main body and is mounted to the mounting holder in a detachable manner.

BRIEF DESCRIPTION OF DRAWINGS

FIGS. 4 (a) and (b) are a plan view and a bottom view showing an electrode sheet of the biomedical electrode pad of the embodiment.

FIGS. 10 (a), (b), and (c) are views illustrating the configuration of the casing of the biological signal processing device of the embodiment and two other types of configuration as examples.

DESCRIPTION OF EMBODIMENTS

Figure 1A:
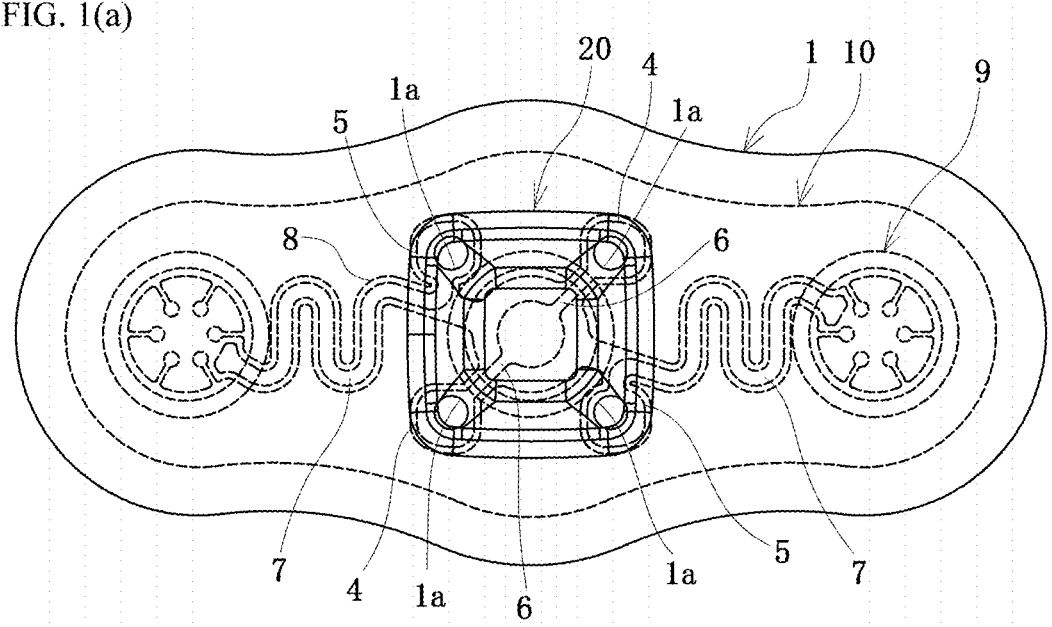
FIGS. 1 (a), (b), and (c) are a plan view, a front view, and a bottom view schematically showing one embodiment of a biomedical electrode pad of the present invention.
Figure 1B:
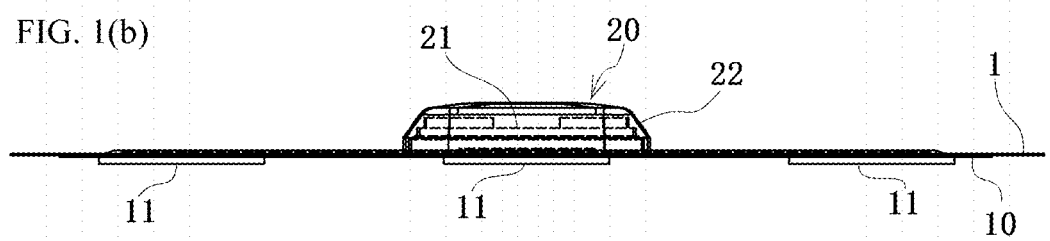
Figure 1C:
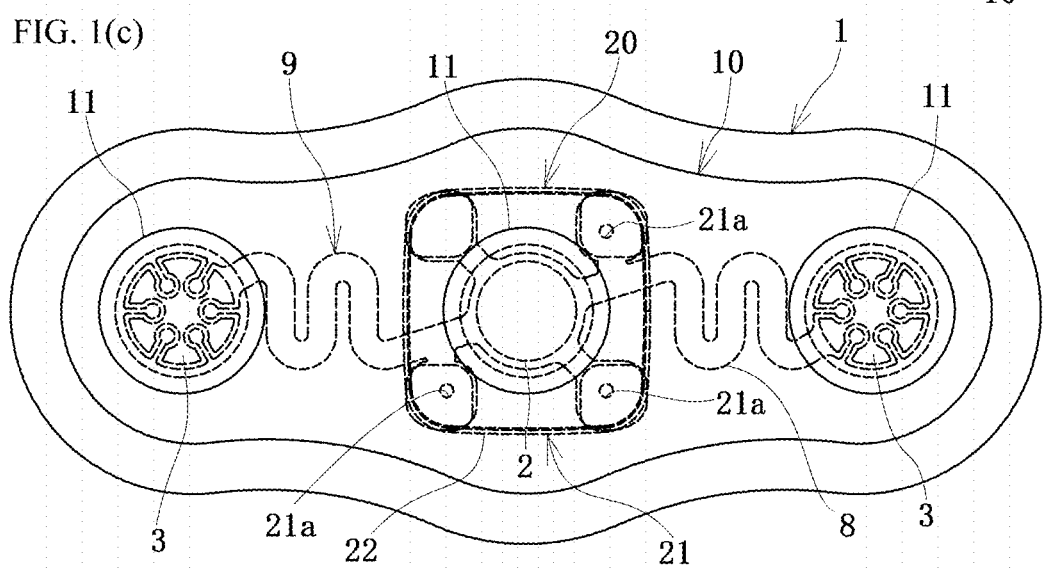
Figure 2:
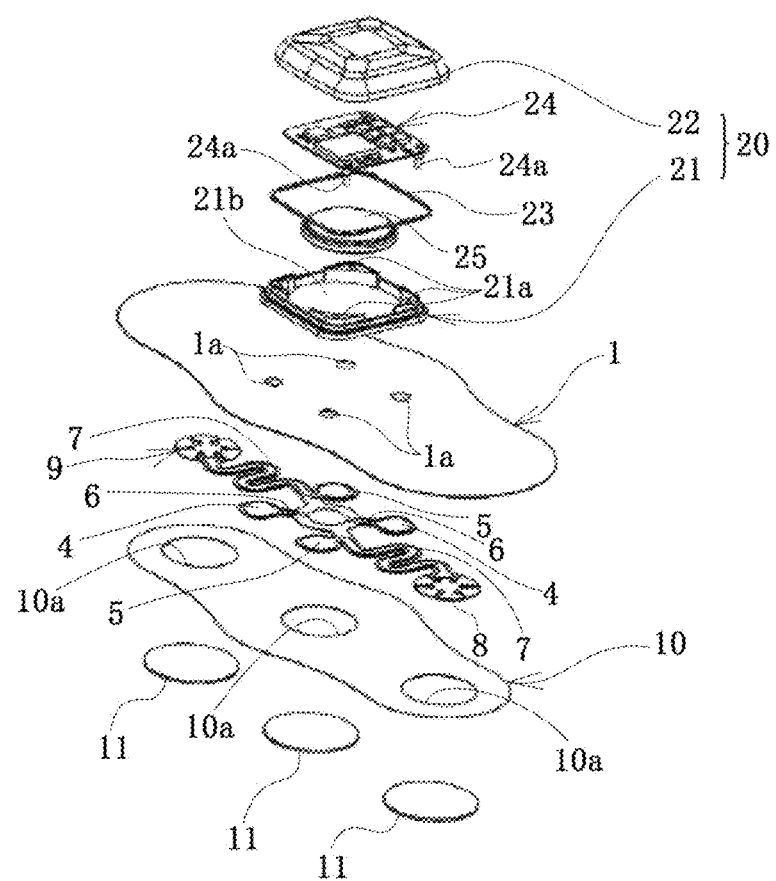
FIG. 2 is an exploded perspective view showing the configuration of the biomedical electrode pad of the embodiment along with the configuration of one embodiment of a biological signal processing device of the present invention that is combined with the biomedical electrode pad.
Figure 3A:
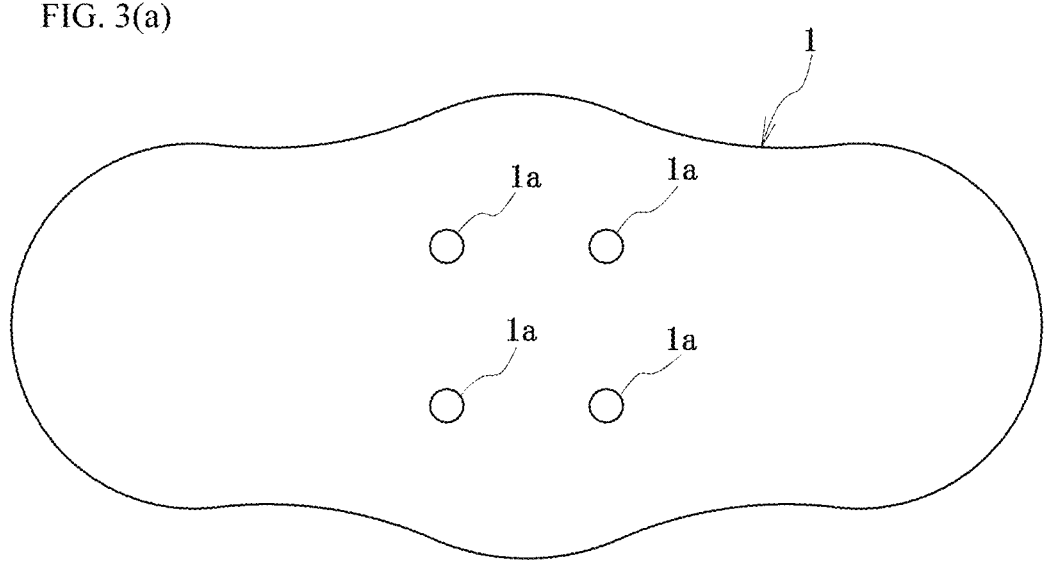
FIGS. 3 (a) and (b) are plan views respectively showing an attachment sheet and a cover sheet of the biomedical electrode pad of the embodiment.
Figure 3B:
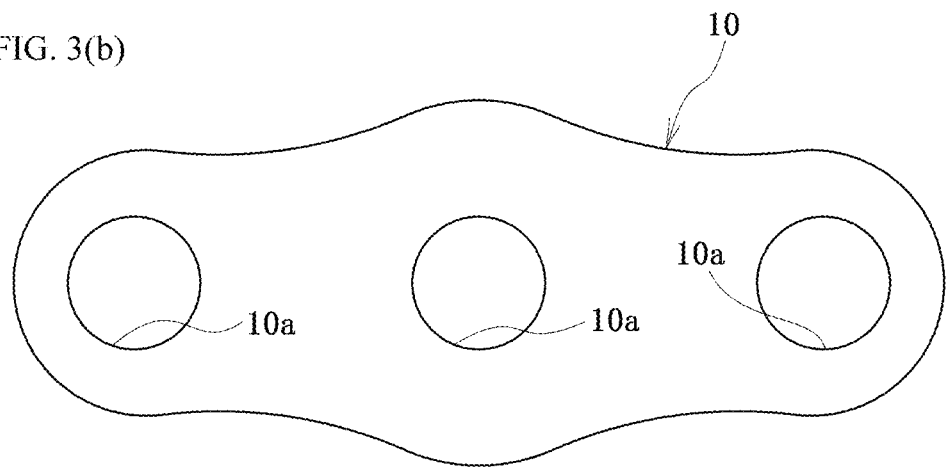

Embodiments of the present invention will be described in detail below based on the drawings. Here, FIG. 1 (a), FIG. 1 (b), and FIG. 1 (c) are a plan view, a front view, and a bottom view schematically showing one embodiment of a biomedical electrode pad of the present invention. FIG. 2 is an exploded perspective view showing the configuration of the biomedical electrode pad of the embodiment along with the configuration of one embodiment of a biological signal processing device of the present invention that is combined with the biomedical electrode pad. FIG. 3 (a) and FIG. 3 (b) are plan views respectively showing an attachment sheet and a cover sheet of the biomedical electrode pad of the embodiment. FIG. 4 (a) and FIG. 4 (b) are a plan view and a bottom view showing an electrode sheet of the biomedical electrode pad of the embodiment.

The biomedical electrode pad of this embodiment is attached to the skin of a subject as a living body and used to detect electrocardiographic signals as biological electrical signals from the skin. This biomedical electrode pad includes: a resin attachment sheet 1 of a substantially elliptical shape bulging toward both sides at a central part that is elastically stretchable, contractible, and bendable, has an electrically insulating property, and has, on a back surface side, an adhesive surface suitable to be attached to the skin of a living body; an indifferent electrode 2 that is located at the central part on the back surface side of the attachment sheet 1 and exposed on the back surface side; two detecting electrodes 3 that are located at each end on the back surface side of the attachment sheet 1, side by side with the indifferent electrode 2 on the same straight line, and exposed on the back surface side; two connecting parts 4 and two connecting parts 5 making pairs in intersecting directions, with the indifferent electrode 2 interposed between each pair of connecting parts, that are located at the central part on the back surface side of the attachment sheet 1, near the indifferent electrode 2, and covered with electrical insulation while being exposed toward the front surface side through openings 1a of the attachment sheet 1; and four electrode connecting wires 6, 7 making two pairs that are located on the back surface side of the attachment sheet 1 and covered with electrical insulation, and that each electrically connect one of the indifferent electrode 2 and the two detecting electrodes 3 to one of the four connecting parts 4, 5 making two pairs. The indifferent electrode 2 and the two detecting electrodes 3 are provided on the back surface side of the attachment sheet 1 as a plurality of electrodes that are located apart from one another. The electrode connecting wires 6 between the indifferent electrode 2 and the two connecting parts 4 extend in a straight line by obliquely crossing the central part on the back surface side of the attachment sheet 1. The electrode connecting wires 7 between each of the two detecting electrodes 3 and the corresponding ones of the two connecting parts 5 are longer than the electrode connecting wires 6, and extend by bending in a bellows shape along a back surface of the attachment sheet 1 in such a manner as to be stretchable and contractible as well as bendable in a direction perpendicular to the plane of the attachment sheet 1.

Here, the indifferent electrode 2 and the two detecting electrodes 3 are formed by conductive layers on a back surface of a resin layer 8 that is elastically stretchable, contractible, and bendable and has an electrically insulating property. The four connecting parts 4, 5 making two pairs and the four electrode connecting wires 6, 7 making two pairs are each formed by a conductive layer on a front surface of the resin layer 8. The indifferent electrode 2 is connected to the two connecting parts 4 by the two straight electrode connecting wires 6 that obliquely cross the central part on the back surface side of the attachment sheet 1, a circular wire at the center that connects these electrode connecting wires 6 to each other, and a plurality of via-hole conductors (not shown) that are provided in this circular wire and extend through the resin layer 8. The two detecting electrodes 3 are connected to the two connecting parts 5 by the two electrode connecting wires 7 and a plurality of via-hole conductors (not shown) that are provided at a leading end of each electrode connecting wire 7 and extend through the resin layer 8. These components constitute an electrode sheet 9.

The resin layer 8 may be formed by, for example, a polyimide sheet, and the conductive layers constituting the indifferent electrode 2 and the two detecting electrodes 3 on a back side of the resin layer 8, and the conductive layers constituting the four connecting parts 4, 5 making two pairs and the four electrode connecting wires 6, 7 making two pairs on a front side of the resin layer 8 may be each formed by, for example, carbon printing, copper plating, copper foil application, silver plating, or silver foil application. Alternatively, the resin layer 8 may be formed by, for example, a polyethylene terephthalate (PET) film, and the conductive layers constituting the four connecting parts 4, 5 making two pairs and the four electrode connecting wires 6, 7 making two pairs on the front side of the resin layer 8 may be each formed by, for example, carbon printing, copper plating, or copper foil application, while the conductive layers constituting the indifferent electrode 2 and the two detecting electrodes 3 on the back side of the resin layer 8 may be formed by, for example, silver plating or silver oxide plating that makes these electrodes less prone to oxidation on contact with the skin.

In the biomedical electrode pad of this embodiment, the electrode sheet 9 is disposed on the adhesive surface of the back surface of the attachment sheet 1, with a front surface side of the electrode sheet 9 facing the back surface of the attachment sheet 1. Further, a cover sheet 10 is stuck on the adhesive surface of the attachment sheet 1 over the electrode sheet 9, and the connecting parts 4, 5 and the electrode connecting wires 6, 7 are fixed to the attachment sheet 1 while being covered with the cover sheet 10. The cover sheet 10 has smaller outside dimensions than the attachment sheet 1 such that the adhesive surface at a peripheral portion of the attachment sheet 1 is exposed, and has circular openings 10a through which the indifferent electrode 2 and the detecting electrodes 3 are respectively exposed.

In the biomedical electrode pad of this embodiment, the two detecting electrodes 3 are each provided with radial incisions to help them deform along the skin. A circular conductive gel sheet 11 larger than each of the indifferent electrode 2, the two detecting electrodes 3, and the openings 10a of the cover sheet 10 through which these electrodes are exposed is disposed as a layer on each of the indifferent electrode 2 and the detecting electrodes 3 over the cover sheet 10, and thus the indifferent electrode 2 and the detecting electrodes 3 are each covered with a conductive gel of the conductive gel sheet 11.

Further, in the biomedical electrode pad of this embodiment, protrusions at four corners of a lower surface of a lower casing part 21 constituting a part of a casing 20 are positioned and adhesively fixed to the front surface side of the attachment sheet 1, at positions corresponding to the four connecting parts 4, 5 of the electrode sheet 9, such that three through-holes 21a of the lower casing part 21 respectively face three of the four openings 1a through which the four connecting parts 4, 5 are respectively partially exposed toward the front side of the attachment sheet 1. There is a gap left between the lower surface of the lower casing part 21 and the front surface of the attachment sheet 1, except for the protrusions at the four corners that are bonded to the front surface of the attachment sheet 1, to facilitate release of perspiration having been produced from the skin of a subject and passed through the attachment sheet 1.

The casing 20 constitutes a part of the biological signal processing device of the embodiment, and the biological signal processing device of the embodiment is combined with the biomedical electrode pad of the embodiment to constitute a Holter electrocardiograph.

Figure 5:
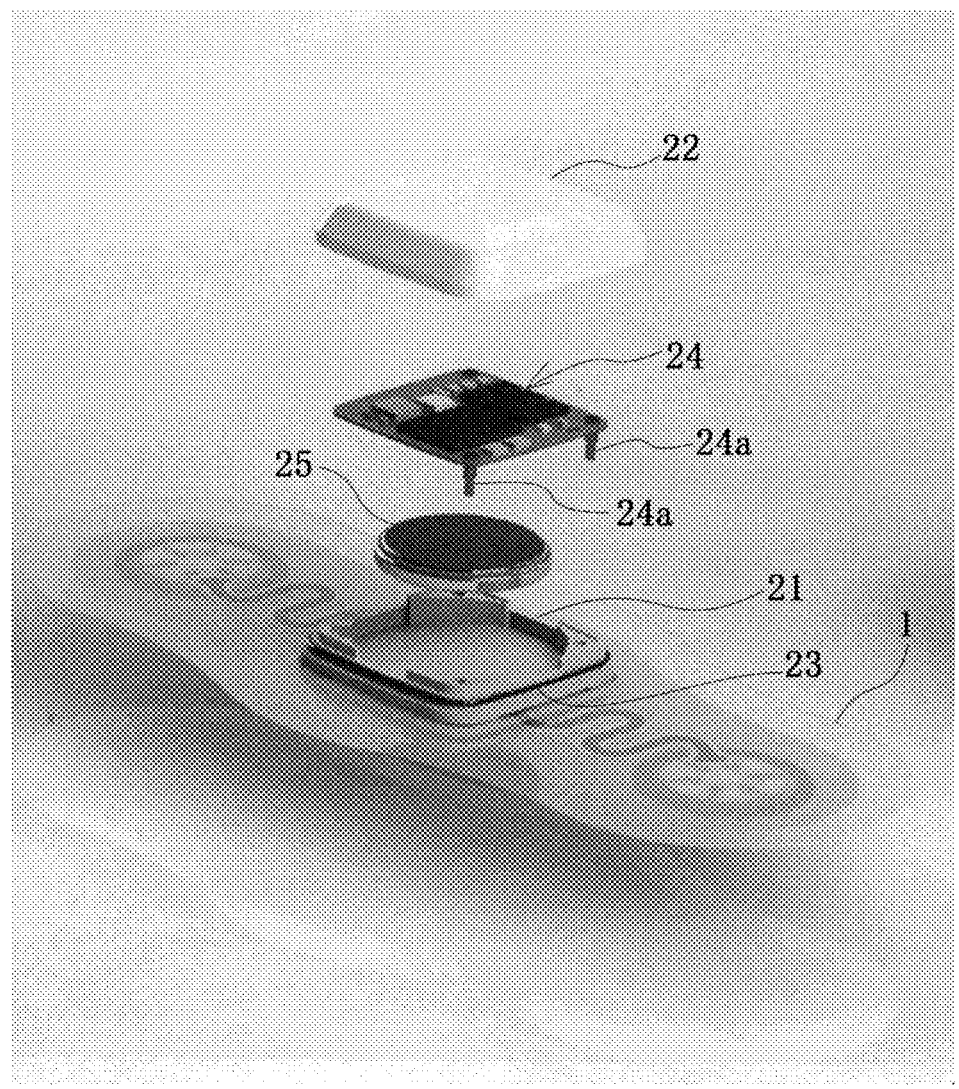
FIG. 5 is an exploded perspective view showing the configuration of the biological signal processing device of the embodiment, in a state where a lower casing part of the biological signal processing device is anchored to a front surface side of the attachment sheet of the biomedical electrode pad of the embodiment.
Figure 6A:
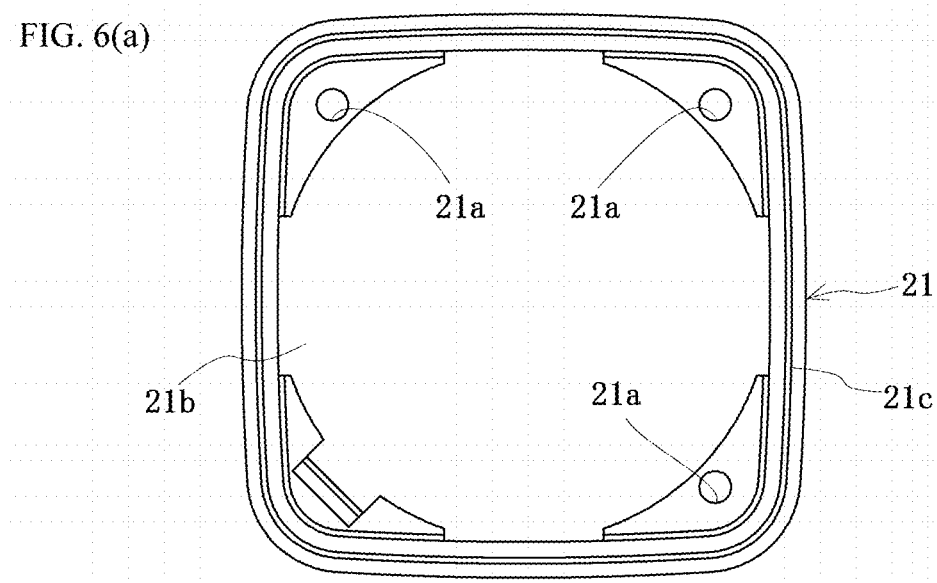
FIGS. 6 (a), (b), and (c) are a plan view, a front view, and a bottom view showing the lower casing part constituting a part of a casing of the biological signal processing device of the embodiment.
Figure 6B:
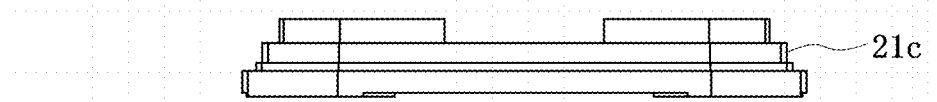
Figure 6C:
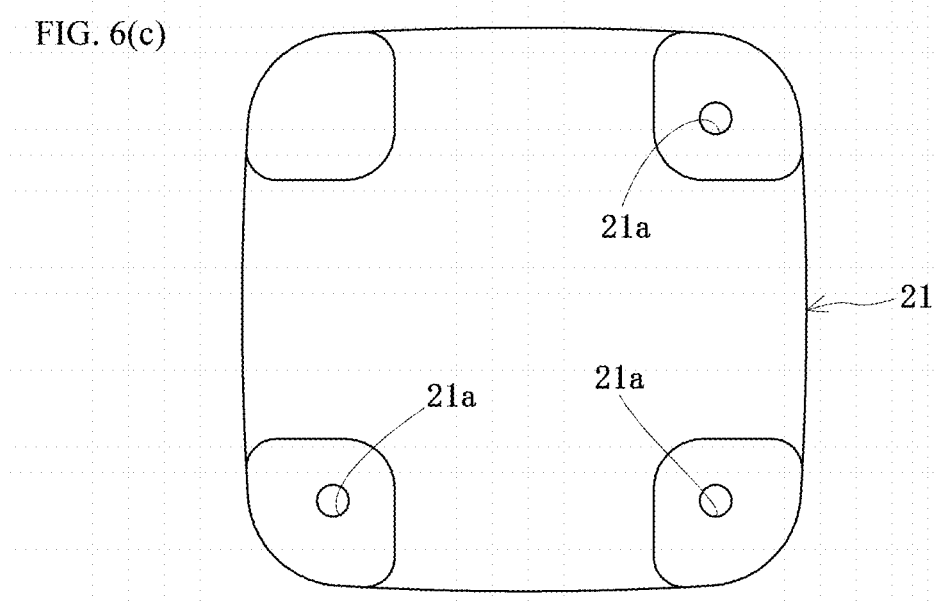
Figure 7A:
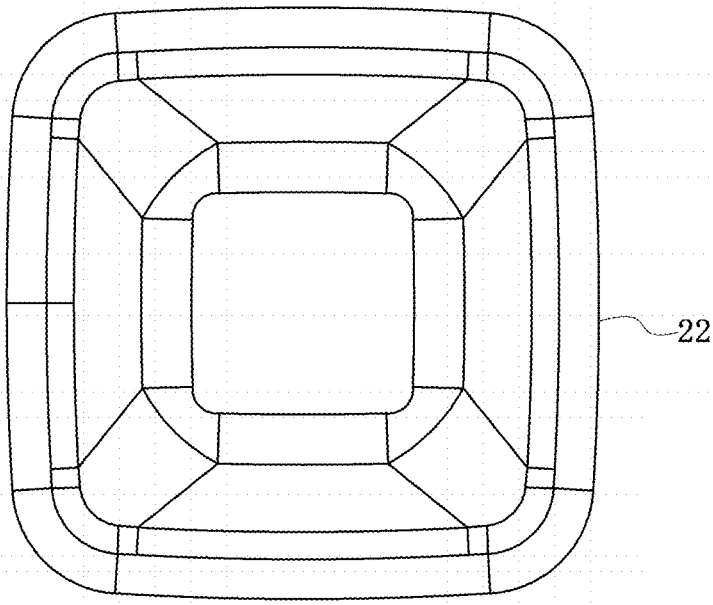
FIGS. 7 (a), (b), and (c) are a plan view, a front view, and a bottom view showing an upper casing part constituting a part of the casing of the biological signal processing device of the embodiment.
Figure 7B:
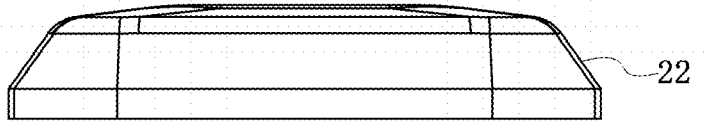
Figure 7C:
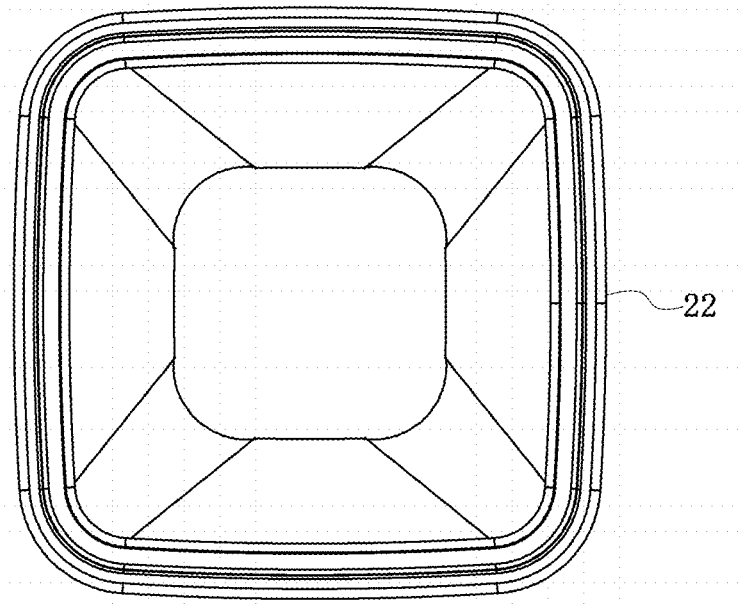
Figure 8A:
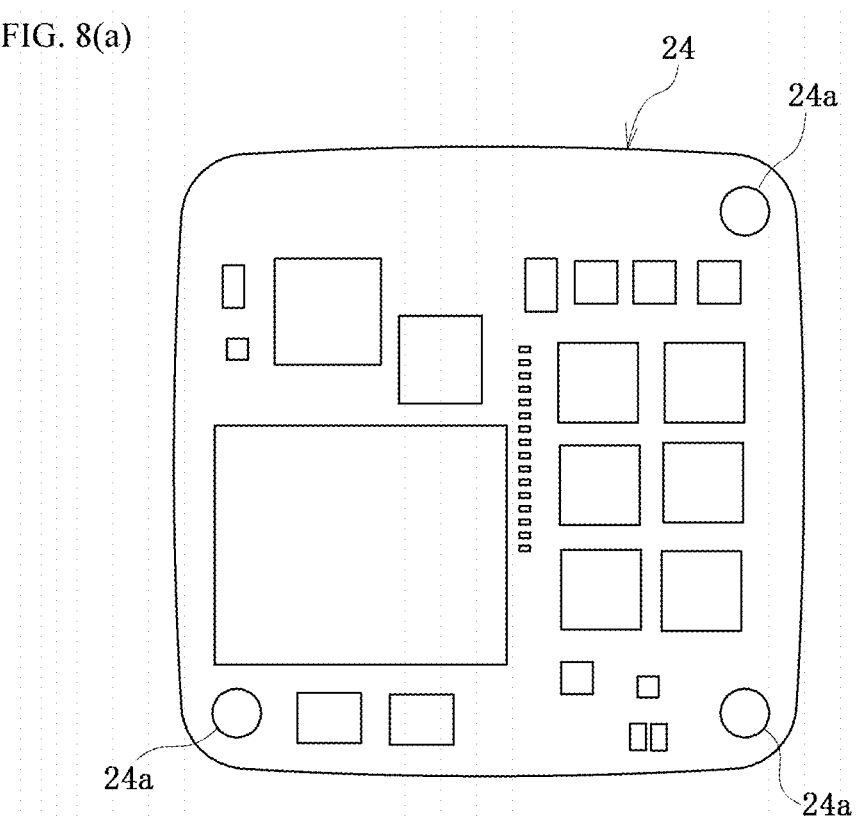
FIGS. 8 (a) and (b) are a plan view and a bottom view showing a biological signal processing circuit board of the biological signal processing device of the embodiment along with contact pins as connecting members that are erected on the biological signal processing circuit board.
Figure 8B:
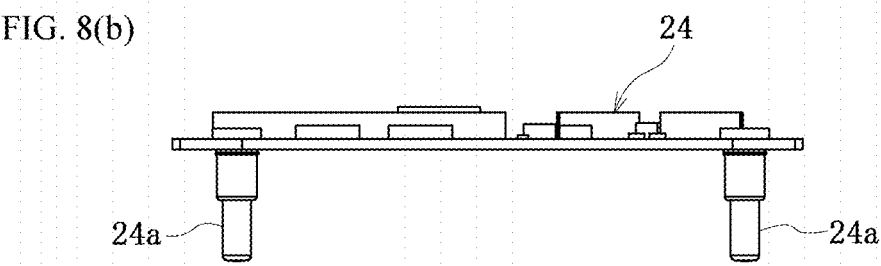
Figure 9:
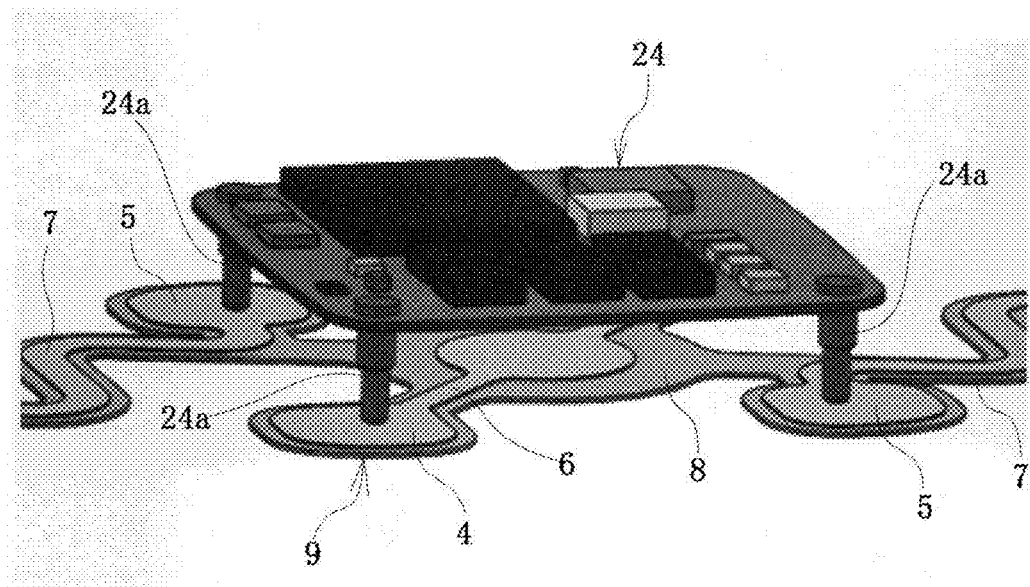
FIG. 9 is a perspective view showing a connected state of the contact pins of the biological signal processing circuit board and connecting parts of the electrode sheet.

FIG. 5 is an exploded perspective view showing the configuration of the biological signal processing device of the embodiment, in a state where the lower casing part 21 of the biological signal processing device is anchored to the front surface side of the attachment sheet 1 of the biomedical electrode pad of the embodiment. FIG. 6 (a), FIG. 6 (b), and FIG. 6 (c) are a plan view, a front view, and a bottom view showing the lower casing part 21 constituting a part of the casing 20 of the biological signal processing device of the embodiment. FIG. 7 (a), FIG. 7 (b), and FIG. 7 (c) are a plan view, a front view, and a bottom view showing an upper casing part 22 constituting the casing 20 along with the lower casing part 21.

As shown in FIGS. 6 (a) to (c), the lower casing part 21 has a substantially square trapezoidal shape with a circular depressed portion 21b at a central part. The through-holes 21a extending through the lower casing part 21 in an up-down direction are formed at three of the protrusions at the four corners surrounding the depressed portion 21b, and an electrode plate (not shown) for connecting to a battery to be described later is provided at the other protrusion. A stepped portion 21c extending along the entire circumference is formed around the lower casing part 21, and a seal ring 23 made of an elastic material is fitted on the stepped portion 21c as shown in FIG. 2 and FIG. 5.

As shown in FIGS. 7 (a) to (c), the upper casing part 22 has a shape of a substantially square lid that is concave on a lower side. An inner circumferential surface of a lower portion of the upper casing part 22 is engaged with a lower portion of the lower casing part 21 including the stepped portion 21c to form the casing 20. The seal ring 23 is squeezed between the upper casing part 22 and the lower casing part 21, and an inside of the casing 20 is liquid-tightly sealed by the seal ring 23.

As shown in FIG. 2 and FIG. 5, a biological signal processing circuit board 24 and a battery 25 of, for example, button type are housed inside the casing 20. The biological signal processing circuit board 24 is a microcomputer composed of a substantially square printed wiring board and electronic components mounted thereon including IC chips and the like, such as a central processing unit (CPU), a memory, and an input-output circuit. The biological signal processing circuit board 24 acts as a Holter electrocardiograph based on a given program, and records electrocardiographic signals input from the indifferent electrode 2 and the detecting electrodes 3 by repeatedly rewriting them, for example, continuously for 24 hours or at few-hour intervals, while continuously analyzing the waveforms of these electrocardiographic signals. When a specific waveform occurs in the electrocardiographic signals, the biological signal processing circuit board 24 outputs an electrocardiogram of the electrocardiographic signals recorded for a certain period of time including that waveform, along with the time of recording, for example, by wirelessly transmitting it or recording it on a removable recording medium, such as a memory card, in order to notify of the occurrence. The battery 25 is disposed inside the casing 20 in a removable manner, and supplies the biological signal processing circuit board 24 with electricity that at least makes the above operation possible.

Here, to establish electrical connection between the input-output circuit of the microcomputer and the connecting parts 5 that are connected to the indifferent electrode 2 and the two detecting electrodes 3 through the electrode connecting wires 6, 7, three contact pins 24a are provided so as to protrude on a lower surface of the biological signal processing circuit board 24, respectively at three of the four corners thereof, as connecting members that extend through the lower casing part 21 and the central part of the attachment sheet 1 and are electrically connected to at least either the biological signal processing circuit board 24 or the connecting parts 5 in a separable manner. These three contact pins 24a are respectively inserted in an extractable manner into the three through-holes 21a extending through the lower casing part 21 in the up-down direction and pass through the openings 1a of the attachment sheet 1 to come into contact with three of the four connecting parts 5.

Of the three contact pins 24a, the two contact pins 24a that are located at the corners on a diagonal line of the biological signal processing circuit board 24 are electrically connected to the two connecting parts 5 that are connected to the two detecting electrodes 3, while the one contact pin 24a located at another corner is electrically connected to one of the two connecting parts 5 that are connected to the indifferent electrode 2.

The reason why two connecting parts 5 connected to one indifferent electrode 2 are provided is as follows: If the two through-holes 21a on a diagonal line of the lower casing part 21 face the two connecting parts 5 connected to the two detecting electrodes 3 at the time of adhesively fixing the lower casing part 21 to the attachment sheet 1, even when the lower casing part 21 is turned 180 degrees, the other through-hole 21a faces one of the two connecting parts 5 connected to the indifferent electrode 2. Therefore, housing the biological signal processing circuit board 24 into the casing 20 in such a direction that the three contact pins 24a enter the three through-holes 21a of the lower casing part 21 can reliably connect these three contact pins 24a respectively to the predetermined connecting parts 5.

In the biomedical electrode pad of the embodiment, when the attachment sheet 1 is stuck on and attached to an electrocardiographic signal detecting position in the skin of a subject through the adhesive surface on the back surface side of the attachment sheet 1, the one indifferent electrode 2 that is located at the central part on the back surface side of the attachment sheet 1 and exposed on the back surface side, and the two detecting electrodes 3 that are located at each end of the attachment sheet 1 and exposed on the back surface side detect electrocardiographic signals from the skin of the subject. These electrocardiographic signals are transmitted by the electrode connecting wires 6, 7 that are located on the back surface side of the attachment sheet 1 and covered with electrical insulation to the four connecting parts 4, 5 making two pairs that are located at the central part on the back surface side of the attachment sheet 1, near the indifferent electrode 2, and covered with electrical insulation, and are then output toward the front surface side of the attachment sheet 1 by those portions of the connecting parts 4, 5 that are exposed through the openings 1a of the attachment sheet 1.

Since the attachment sheet 1 of the biomedical electrode pad of the above embodiment is elastically stretchable, contractible, and bendable and has an electrically insulating property, the attachment sheet 1 remains in close contact with the skin by stretching, contracting, and/or bending so as to follow changes in shape of the limb due to body movement. Moreover, since the electrode connecting wires 7 between each of the two detecting electrodes 3 and the corresponding ones of the two connecting parts 5 extend by bending in a bellows shape in a stretchable, contractible, and bendable manner, the electrode connecting wires are less likely to break by undergoing excessive local deformation when the attachment sheet 1 stretches, contracts, and/or bends so as to follow changes in shape of the limb due to body movement.

Therefore, even when the attachment sheet 1 is expanded compared with the conventional one to broaden the range of detecting electrocardiographic signals, the biomedical electrode pad of the embodiment can continuously detect electrocardiographic signals from the skin by the indifferent electrode 2 and the detecting electrodes 3 for a long period of time, regardless of changes in shape of the limb due to body movement.

In the biological signal processing device of the above embodiment, when the elastically stretchable and contractible attachment sheet 1 of the biomedical electrode pad is attached to an electrocardiographic signal detecting position in the skin of a subject through the adhesive surface on the back surface side of the attachment sheet 1, the biological signal processing circuit board 24 housed inside the casing 20 fixed at the central part on the front surface side of the attachment sheet 1 is electrically connected to each of the indifferent electrode 2 and the two detecting electrodes 3 provided on the back surface side of the biomedical electrode pad through the connecting pins 24a extending through the casing 20 and the central part of the attachment sheet 1 and the electrode connecting wires 6, 7 on the electrode sheet 9. By being supplied with electricity from the battery 25 that is also housed inside the casing 20, the biological signal processing circuit board 24 performs the process of analyzing and recording the electrocardiographic signals detected from the skin of the subject by the indifferent electrode 2 and the detecting electrodes 3, and outputs the processing result to the outside by at least either recording it on a recording medium, such as a memory card, or wirelessly transmitting it.

Thus, in the biological signal processing device of the embodiment, the biological signal processing circuit board 24 is housed inside the casing 20 fixed to the front surface side of the elastically stretchable and contractible attachment sheet 1 of the biomedical electrode pad, supplied with electricity from the battery 25, and electrically connected to each of the indifferent electrode 2 and the two detecting electrodes 3 on the back surface side of the attachment sheet 1 through the connecting pins 24a extending through the casing 20 and the central part of the attachment sheet 1, and through the connecting parts 5 and the electrode connecting wires 6, 7 on the back surface side of the attachment sheet 1. Since wires connecting the biological signal processing circuit board and the biomedical electrode pad to each other are not exposed to the outside, the biomedical electrode pad is unlikely to come easily off the skin due to body movement, such as movement of the arm or twisting of the body, and therefore can continuously detect electrocardiographic signals from the skin by the indifferent electrode 2 and the detecting electrodes 3 for a long period of time, regardless of changes in shape of the limb due to body movement.

The combination of the biomedical electrode pad of the embodiment and the biological signal processing device of the embodiment, despite using the biomedical electrode pad of which the attachment sheet 1 is expanded compared with the conventional one to broaden the range of detecting electrocardiographic signals, can continuously detect electrocardiographic signals from the skin by the indifferent electrode 2 and the detecting electrodes 3 for a long period of time, regardless of changes in shape of the limb due to body movement, by effectively preventing the biomedical electrode pad from coming off the skin.

Moreover, in the biomedical electrode pad of the embodiment, the conductive gel sheet 11 is disposed as a layer on each of the indifferent electrode 2 and the two detecting electrodes 3. Thus, the electrical resistance between the electrodes 2, 3 and the skin can be reduced by the conductive gel sheet 11 to raise the electrocardiographic signal detection level. In the biomedical electrode pad of this embodiment, either each of the indifferent electrode 2 and the detecting electrodes 3 or the conductive gel sheets 11 may be disposed on the skin side so as to come into contact with the skin.

Furthermore, in the biomedical electrode pad of this embodiment, the cover sheet 10 is stuck on the back surface side of the attachment sheet 1, and the electrode connecting wires 6, 7 and the connecting parts 5 are fixed to the attachment sheet 1 by being covered with the cover sheet 10. The cover sheet 10 has smaller dimensions than the attachment sheet 1 such that the adhesive surface at the peripheral portion of the attachment sheet 1 is exposed, and has the openings 10a through which the indifferent electrode 2 and the two detecting electrodes 3 are respectively entirely exposed. Thus, the electrode connecting wires 6, 7 and the connecting parts 5 can be easily covered with electrical insulation. At the same time, the electrode connecting wires 6, 7 and the connecting parts 5 can be easily prevented from coming off or shifting over the attachment sheet 1 regardless of the attachment sheet 1 stretching and contracting according to changes in shape of the limb due to body movement.

In the biological signal processing device of the embodiment, the biological signal processing circuit board 24 has the contact pins 24a that are erected on the lower surface of the biological signal processing circuit board 24 and extend through the casing 20 and the central part of the attachment sheet 1 in an insertable and extractable manner to electrically come into contact with the connecting parts 5. Thus, the battery 25 and a recording medium can be easily replaced by attaching and detaching the biological signal processing circuit board 24 to and from the casing 20.

In the biological signal processing device of the above embodiment, as shown at an upper part and a lower part of FIG. 10 (*a*), the casing 20 has the lower casing part 21 that is fixed to the attachment sheet 1 and the upper casing part 22 that is mounted to the lower casing part 21 in a detachable manner, and the lower casing part 21 and the upper casing part 22 house the biological signal processing circuit board 24. Alternatively, as shown at an upper part and a lower part of FIG. 10 (*b*), the casing 20 of the biological signal processing device of the present invention may have a mounting holder 26 that is fixed to the attachment sheet 1, and a casing main body 27 that houses the biological signal processing circuit board 24 and is mounted to the mounting holder 26 in a detachable manner, or, as shown at an upper part and a lower part of FIG. 10 (*c*), the casing 20 may have a mounting holder 28 that is fixed to the attachment sheet 1, a casing main body 30 that houses the biological signal processing circuit board 24, and a casing cover 29 that covers the casing main body 30 and is mounted to the mounting holder 28 in a detachable manner.

Figure 11A:
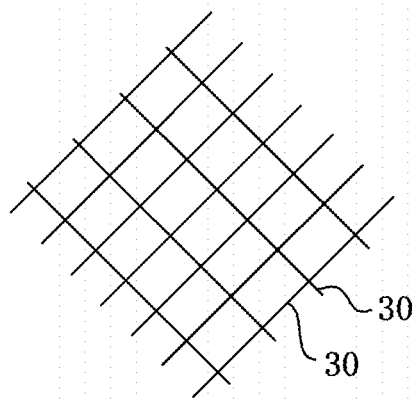
FIGS. 11 (a), (b), and (c) are views partially illustrating, as examples, three other types of configuration of electrode connecting wires of the biomedical electrode pad of the embodiment.
Figure 11B:
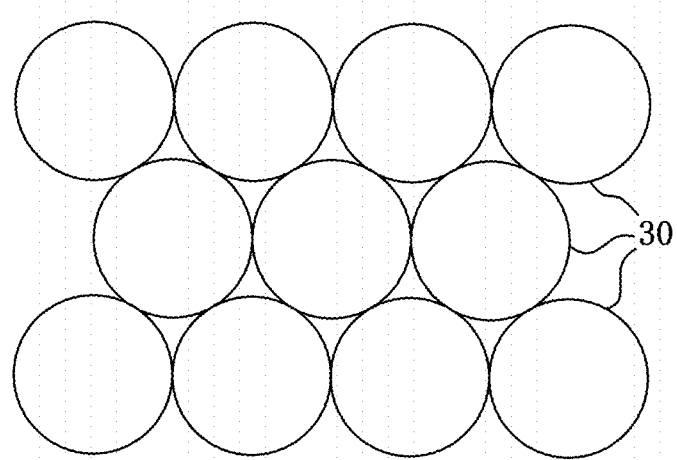
Figure 11C:
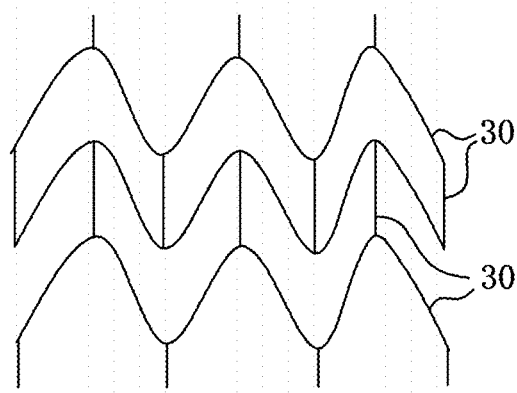

FIG. 11 (*a*), FIG. 11 (*b*), and FIG. 11 (*c*) are views partially illustrating, as examples, three other types of configuration of the electrode connecting wires 6, 7 of the biomedical electrode pad of the above embodiment. The electrode connecting wire of FIG. 11 (*a*) employs a large number of linear fibrous conductors 30, formed by copper wires or the like, that intersect one another and are electrically connected to one another at intersections by welding or the like to form a mesh. The electrode connecting wire of FIG. 11 (*b*) employs a large number of ring-shaped fibrous conductors 30, formed by copper wires or the like, that are combined with one another and electrically connected to one another at contact points by welding or the like to form a chain. The electrode connecting wire of FIG. 11 (*c*) employs a large number of wavy fibrous conductors 30, formed by copper wires or the like, that are coupled to one another by a large number of linear fibrous conductors 30, also formed by copper wires or the like, and electrically connected to one another at coupling points to form a cloth, such as a woven cloth or a non-woven cloth. Electrode connecting wires of one of these types extend in a stretchable, contractible, and bendable manner as the electrode connecting wires 6 between the indifferent electrode 2 and the two connecting parts 4 and/or the electrode connecting wires 7 between the two detecting electrodes 3 and the two connecting parts 5.

While the present invention has been described above based on the examples shown in the drawings, the present invention is not limited to these examples but can be changed as necessary within the scope of the description of the claims. For example, in the biomedical electrode pad of the present invention, only the two detecting electrodes at both ends may be provided by omitting the indifferent electrode, or the number of the detecting electrodes may be increased to three or more, and in that case, the indifferent electrode at the central part may be changed to a detecting electrode. The plurality of electrodes need not be disposed side by side on the same straight line. Further, at least either the electrode connecting wires 6 or 7 may be wires formed by, for example, a flake-shaped conductor made of a conductive rubber-like elastic material obtained by diffusing fibrous conductors, such as carbon nanotubes (CNTs), inside a rubber-like base material, instead of the examples shown in FIG. 4 or FIG. 11 (*a*) to FIG. 11 (*c*). The biomedical electrode pad of the present invention can also be used to detect myoelectric signals instead of or in addition to electrocardiographic signals. The biomedical electrode pad of the present invention may be connected to an ordinary biological signal processing device through a lead instead of being combined with the biological signal processing device of the present invention.

In the biological signal processing device of the present invention, for example, the connecting members may extend through and be fixed to the casing and the attachment sheet, and lower end portions of the connecting members may be always in contact with the connecting parts while upper end portions thereof may be in contact with a circuit pattern of the biological signal processing circuit board in a separable manner. The biological signal processing device of the present invention may be equipped with an IC chip constituting a wireless communication circuit based on standards of wireless LAN, such as Wi-Fi, and may transmit biological signals input from the biomedical electrode pad to an external transmission device through this wireless communication circuit, and a computer connected to this external communication device may perform processing including recording and analyzing the biological signals. The casing of the biological signal processing device of the present invention may be fixed to an attachment sheet of an ordinary biomedical electrode pad instead of being fixed to the attachment sheet of the biomedical electrode pad of the present invention.

INDUSTRIAL APPLICABILITY

As has been described above, even when the attachment sheet is expanded compared with the conventional one to broaden the range of detecting biological signals, the biomedical electrode pad of the present invention can continuously detect biological signals from the skin by the plurality of electrodes for a long period of time, regardless of changes in shape of the limb due to body movement.

In the biological signal processing device of the present invention, since the wires connecting the biological signal processing circuit board and the biomedical electrode pad to each other are not exposed to the outside, the biomedical electrode pad is unlikely to come easily off the skin due to body movement, such as movement of the arm or twisting of the body, and therefore can continuously detect biological signals from the skin by the plurality of electrodes for a long period of time, regardless of changes in shape of the limb due to body movement.

The combination of the biomedical electrode pad of the present invention and the biological signal processing device of the present invention, despite using the biomedical electrode pad of which the attachment sheet is expanded compared with the conventional one to broaden the range of detecting biological signals, can continuously detect biological signals from the skin by the plurality of electrodes for a long period of time, regardless of changes in shape of the limb due to body movement, by effectively preventing the biomedical electrode pad from coming off the skin.

REFERENCE SIGNS LIST

1 Attachment sheet
1a Opening
2 Indifferent electrode
3 Detecting electrode
4, 5 Connecting part
6, 7 Electrode connecting wire
8 Resin layer
9 Electrode sheet
10 Cover sheet
10a Opening
11 Conductive gel sheet
20 Casing
21 Lower casing part
21a Through-hole
21b Depressed portion
21c Stepped portion
22 Upper casing part
23 Seal ring
24 Biological signal processing circuit board
24a Connecting pin
25 Battery
26, 28 Mounting holder
27, 30 Casing main body
29 Casing cover
30 Fibrous conductor

The invention claimed is:

1. A system comprising:
a biomedical electrode pad that is configured to be attached to skin of a living body and configured to detect biological electrical signals from the skin, the biomedical electrode pad comprising:
an attachment sheet that is elastically stretchable and contractible, has an electrically insulating property, and has, on a first side, an adhesive surface configured to be attached to the skin of a living body;
a plurality of electrodes that are located apart from one another on the first side of the attachment sheet and exposed on the first side;
a set of four connecting parts that are circumferentially located around a central part on the first side of the attachment sheet and covered with electrical insulation while being exposed toward a second side of the attachment sheet through openings of the attachment sheet; and
electrode connecting wires that are located on the first side of the attachment sheet and covered with electrical insulation, and that electrically connect respective ones of the plurality of electrodes with corresponding ones of the four connecting parts,
wherein at least one of the electrode connecting wires extends in a stretchable, contractible, and bendable manner,
a biological signal processing device, comprising:
a casing that is adhesively and integrally fixed to four portions corresponding to the four connecting parts exposed from the second side of the attachment sheet of the biomedical electrode pad;
a biological signal processing circuit board that is housed inside the casing and electrically connected to each of the plurality of electrodes through a connecting member extending through the casing and the four portions of the attachment sheet, and that processes biological signals detected by the plurality of electrodes and outputs a processing result; and
a battery that is housed inside the casing and supplies electricity to the biological signal processing circuit board,
wherein a plurality of protrusions provided at a lower part of the casing are fixed to the second side of the attachment sheet, and the connecting member extends through the inner portion of at least one of the protrusions.

2. The system according to claim 1, wherein the plurality of electrodes include a plurality of detecting electrodes whose conductive portions are each provided with radial incisions that are configured to permit each of the detecting electrodes to deform along the skin.

3. The system according to claim 2, wherein a conductive gel sheet is disposed as a layer on each of the plurality of electrodes.

4. The system according to claim 1, wherein there is a gap present between a lower surface of a lower casing part of the casing and the second side of the attachment sheet, except for the plurality of protrusions that are fixed to the second side of the attachment sheet.

5. The system according to claim 4, wherein a conductive gel sheet is disposed as a layer on each of the plurality of electrodes.

6. The system according to claim 1, wherein the at least one of the electrode connecting wires that extends in the stretchable, contractible, and bendable manner has a conductor that is bent in a bellows shape.

7. The system according to claim 6, wherein a conductive gel sheet is disposed as a layer on each of the plurality of electrodes.

8. The system according to claim 1, wherein the at least one of the electrode connecting wires that extends in the stretchable, contractible, and bendable manner has fibrous conductors that are in a form of a mesh, a chain, or a cloth.

9. The system according to claim 8, wherein a conductive gel sheet is disposed as a layer on each of the plurality of electrodes.

10. The system according to claim 9, wherein the casing has a lower casing part that is fixed to the attachment sheet and an upper casing part that is mounted to the lower casing part in a detachable manner, and the lower casing part and the upper casing part house the biological signal processing circuit board.

11. The system according to claim 9, wherein the casing has a mounting holder that is fixed to the attachment sheet, and a casing main body that houses the biological signal processing circuit board and is mounted to the mounting holder in a detachable manner.

12. The system according to claim 9, wherein the casing has a mounting holder that is fixed to the attachment sheet, a casing main body that houses the biological signal processing circuit board, and a casing cover that covers the casing main body and is mounted to the mounting holder in a detachable manner.

13. The system according to claim 1, wherein the at least one of the electrode connecting wires that extends in the stretchable, contractible, and bendable manner has a conductor that is made of a conductive elastic material.

14. The system according to claim 1, wherein the plurality of electrodes include an indifferent electrode and a plurality of detecting electrodes.

15. The system according to claim 1, wherein a corresponding conductive gel sheet is disposed as a layer on each of the plurality of electrodes.

16. The system according to claim 1, wherein a cover sheet is stuck on the first side of the attachment sheet, and the electrode connecting wires and the connecting parts are fixed to the attachment sheet by being covered with the cover sheet, the cover sheet having smaller dimensions than the attachment sheet such that the adhesive surface at a peripheral portion of the attachment sheet is exposed, and having openings through which the plurality of electrodes are respectively at least partially exposed.

17. The system according to claim 1, wherein the connecting member extending through the casing and the four portions of the attachment sheet is electrically in contact with at the biological signal processing circuit board in a separable manner.

18. The system according to claim 1, wherein the casing has a lower casing part that is fixed to the attachment sheet and an upper casing part that is mounted to the lower casing part in a detachable manner, and the lower casing part and the upper casing part house the biological signal processing circuit board.

19. The system according to claim 1, wherein the casing has a mounting holder that is fixed to the attachment sheet, and a casing main body that houses the biological signal processing circuit board and is mounted to the mounting holder in a detachable manner.

20. The system according to claim 1, wherein the casing has a mounting holder that is fixed to the attachment sheet, a casing main body that houses the biological signal processing circuit board, and a casing cover that covers the casing main body and is mounted to the mounting holder in a detachable manner.

\* \* \* \* \*